United States Patent
Chabrecek et al.

(10) Patent No.: US 6,436,481 B1
(45) Date of Patent: Aug. 20, 2002

(54) METHOD OF PRODUCING A REACTIVE COATING BY AFTER-GLOW PLASMA POLYMERIZATION

(75) Inventors: Peter Chabrecek, Riehen; Dieter Lohmann, Münchenstein, both of (CH)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 09/331,516

(22) PCT Filed: Dec. 19, 1997

(86) PCT No.: PCT/EP97/07201
§ 371 (c)(1),
(2), (4) Date: Jun. 22, 1999

(87) PCT Pub. No.: WO98/28026
PCT Pub. Date: Jul. 2, 1998

(30) Foreign Application Priority Data

Dec. 23, 1996 (EP) ............................................. 96810890

(51) Int. Cl.[7] .................................................. C08J 7/18
(52) U.S. Cl. ....................... 427/488; 427/491; 428/332; 523/105; 523/106; 523/107; 523/108
(58) Field of Search ................. 523/105–108; 525/937; 427/446–449, 488, 491; 428/220, 332, 333, 336, 338, 341, 410, 411.1, 413, 423.1, 500, 524, 923, 926; 351/160 R, 160 H

(56) References Cited

U.S. PATENT DOCUMENTS

| 4,663,233 | A | * | 5/1987 | Beavers ...................... 428/412 |
|---|---|---|---|---|
| 4,693,799 | A | * | 9/1987 | Yanagihara et al. ......... 204/165 |
| 5,007,928 | A | * | 4/1991 | Okamura et al. ............... 623/6 |
| 5,037,677 | A | * | 8/1991 | Halpern et al. .............. 427/338 |
| 5,080,924 | A | * | 1/1992 | Kamel et al. ................... 427/2 |
| 6,169,127 | B1 | * | 1/2001 | Lohmann et al. ............ 523/106 |

FOREIGN PATENT DOCUMENTS

| WO | WO 89/11500 | 5/1989 |
|---|---|---|
| WO | WO 94/00165 | 5/1993 |
| WO | WO 95/25594 | 5/1993 |
| WO | WO 94/06485 | 9/1993 |

OTHER PUBLICATIONS

Abstract—JP62032884/JP5028108B—Nippon Oil Seal Ind. Co., Ltd.

* cited by examiner

*Primary Examiner*—Paul Thibodeau
*Assistant Examiner*—Monique R. Jackson
(74) *Attorney, Agent, or Firm*—R. Scott Meece; Jian S. Zhou; Richard I. Gearhart

(57) ABSTRACT

The present invention describes coated articles and methods for preparing such articles, wherein the primary coating comprises a plasma-induced polymer carrying reactive groups. The invention further relates to the reaction of said primary coatings carrying reactive groups with monomeric, oligomeric or macromolecular compounds of synthetic, semisynthetic or biological origin to provide hybrid-type coated articles (secondary coatings).

8 Claims, No Drawings

METHOD OF PRODUCING A REACTIVE COATING BY AFTER-GLOW PLASMA POLYMERIZATION

The present invention relates to coated articles wherein the primary coating comprises a polymer carrying reactive groups. The coating is covalently linked to the surface of the article and exhibits a controlled degree of crosslinking. The invention further relates to the reaction of said primary coatings carrying reactive groups with monomeric, oligomeric or macromolecular compounds of synthetic, semisynthetic or biological origin to provide hybrid-type coated articles and to such articles which exhibit desirable characteristics regarding adherence to the substrate, reactivity, lubricity, durability, biocompatibility, (bio)affinity, (bio) activity, permeability, permselectivity for gases, liquids and solutions, and wettability by aqueous solutions, such as human body fluids. More particularly, the present invention relates to an article, such as a biomedical material or article, especially ophthalmic devices and implants such as artificial corneas, intraocular lenses and contact lenses, including an extended-wear contact lens which is at least partially coated. The articles are obtainable by after-glow plasma-induced polymerization of a polymerizable unsaturated compound having reactive groups, preferably polymerizable vinyl or isopropenyl compounds carrying isocyanato, isothiocyanato, glycidyl, anhydride, azlactone or lactone groups under specific plasma conditions. The invention further relates to such articles carrying a laminate coating obtainable by reacting said reactive groups with a monomeric, oligomeric or macromolecular compound of synthetic, semisynthetic or biological origin.

The provision of a coating on a substrate may generally be desirable for a variety of reasons including protection of the substrate and provision of desirable surface characteristics which the substrate material does not exhibit to the required degree. In the case of biomedical devices, such as ophthalmic devices, e.g. contact lenses it is desirable to have surfaces which are readily wettable by an aqueous liquid such as tear fluid and are capable to retain an aqueous fluid layer which prevents eye irritation and is beneficial for the easy movement of the contact lens on the eye which in turn is important for the comfort of the wearer. The sliding motion of the contact lens is facilitated by the presence of a continuous layer of tear fluid on the contact lens, a layer which lubricates the tissue/lens interface. Additionally, the adhesiveness towards proteins, lipids, minerals, cell debris and other spoilations or micro-organisms and the permeability and stability characteristics of the surface of the contact lens having a coating thereon are of great importance. The permeability of the lens material for gases, water and ions which is required especially in the case of extended wear contact lenses must not be impaired by the coating which is provided in order to impart hydrophilicity to the surface. The coating should exhibit thermal, oxidative and hydrolytic stability as well as resistance to formation of deposits from tear components. Moreover, delamination caused by mechanical stress should not happen. It is of particular advantage the coated article can be sterilized by autoclaving without affecting the uniformity, the thickness and the properties of the coating.

Materials with wettable and biocompatible surfaces are highly desirable for many applications. The wettability of materials is strongly dependent on topography, morphology and on the chemical composition of the material surface. In particular, the ability of the surface to hold a continuous layer of an aqueous solution, such as tear fluid for a prolonged period or time (>10 seconds), is affected by the composition of the material surface. Known attempts to solve the wettability problem in the ophthalmic field include methods for the activation of a device surface. The methods being generic, so that the surface of any material with suitable bulk properties can be converted to be receptive for the covalent immobilization of a coating which is highly retentious for aqueous layers.

A number of surface treatment techniques for polymeric materials are known in the art. Chemical Vapor Depostion (CVD), Corona discharge, ozone treatment, flame treatment, acid etching, and a number of other methods intended to achieve chemical modification of the surface. Among the disadvantages of these techniques are the use of elevated temperatures or the use of hazardous chemicals, the often excessive depth of treatment, non-uniformity of treatment at a microscopic level, and often severe etching and pitting that leads to changes in surface topography. The depth of treatment is important because with clear materials such as those required for lenses the optical clarity and surface smoothness become affected after an excessively harsh treatment. Moreover, surfaces thus treated usually contain complex mixtures of polar groups of sometimes limited stability and are often highly crosslinked which considerably affects the overall permeability characteristics.

Treatment of polymeric surfaces by gas plasmas provides the advantages of very low treatment depth, and high uniformity on a microscopic scale. A gas plasma can for example be generated by glow discharge in a gas atmosphere at reduced pressure ("vacuum"). It creates a stable, partially ionized gas that may be utilized for effecting reactions on the surface of the substrate because the gas plasma environment activates even chemical compounds that are unreactive under normal conditions. The treatment intensity at the surface is generally relatively high, and yet the penetration depth of gas plasma treatment is very low, of the order of 5 to 50 nanometers, at a treatment intensity sufficient for useful surface modification. Surface topography and optical clarity do not change unless exposure to the plasma is performed at high energy levels or for periods of time much exceeding the time required for achieving the desired chemical modification of the surface. Glow discharge plasma reactions therefore result in significantly less alteration of the properties of the bulk material as compared to the alternative treatment technologies described above.

Gas plasma techniques can have two types of outcomes. In the first, commonly called plasma surface treatment, the surface of a polymeric material to be treated ("the substrate") is subjected to a plasma established in one or more inorganic vapors or some select organic vapors, and the plasma treatment causes the replacement of some of the original chemical groups on a polymer surface by other, novel groups which are contributed from the plasma gas. For instance, the plasma surface treatment of polytetrafluoroethylene in an ammonia plasma leads to the abstraction of some of the surface fluorine atoms by C—F bond breakage and the incorporation into the modified surface layer of amine groups by C—N bond formation. Plasma surface treatment in an appropriate vapor such as ammonia, oxygen, carbon dioxide, or water vapor, can therefore be used to place on the surface of any polymeric material reactive chemical groups, such as amine, carboxyl, or hydroxyl, suitable for the subsequent covalent immobilization of various molecules. The overall outcome of this technique is a surface functionalization of a substrate material.

The second type of plasma technique is commonly called plasma polymerization and occurs when a discharge is struck in most organic vapors. In contrast to plasma surface treatment, in which less than a monolayer of new material is added, the technique of plasma polymerization leads to the formation of film coatings which can be up to several micrometers thick and can completely mask the substrate.

Plasma polymers are usually covalently bound to the underlying substrate. The covalent attachment of the plasma coating to the bulk material ensures that the plasma polymer does not detach. Furthermore, common plasma polymers are usually highly crosslinked and do not contain leachable low molecular weight fragments which might migrate into body tissue or fluids.

By appropriate choice of the monomer vapor and the plasma conditions, plasma polymer coatings can be fabricated to contain specific, chemically reactive groups which are also suitable for the subsequent chemical attachment of various molecules to the surface. Thus, WO 94/06485 discloses activation of the surface of a polymeric material which does not inherently carry suitable reactive groups by plasma surface treatment, plasma polymerization, or plasma polymerization followed by a subsequent plasma surface treatment. In this way, a composite material, especially a biomedical device, e.g. an ophthalmic device, such as a contact lens can be provided having one or more wettable surfaces capable of holding a continuous layer of aqueous fluid thereon, wherein the composite comprises a carbohydrate which is covalently bound by a hydrolytically stable bond to a plasma surface prepared on the base material.

JP-A-62/032884 discloses a method of immobilizing physiologically active substances comprising applying a plasma to the inner wall of a test tube filled with monomer gas atmosphere of an aldehyde compound or a diisocyanate compound to form aldehyde groups or isocyanate groups on the inner wall face of the test tube, and reacting amino groups of a physiologically active substance (such as an enzyme) with these functional groups to immobilize the active substance onto the inner wall face. According to the general teachings in plasma chemistry, a diisocyanate under plasma conditions can only form a polymer under fragmentation and recombination processes. Therefore, only a low content of intact OCN-groups is expected in said disclosure.

Plasma polymerization as used in the prior art mentioned above is a method wherein the substrate may be located within the plasma zone (so called "in glow") or alternatively outside (below) the plasma zone ("after glow", downstream or remote plasma) and the monomer(s) as well as the plasma gas stream (e.g. $H_2$, He, Ar) are introduced into the plasma zone.

While polymeric coatings prepared by this so-called "in-glow" plasma polymerization may have suitable surface properties they do not consist of chains with regular repeating units but tend to form an irregular three-dimensional crosslinked network; see A. P. Ameen et al., Polymer, Vol. 35 (1994) p. 4382. Organic compounds used as monomers are usually heavily fragmented by the plasma and form a complex mixture of various ions, atoms, radicals and other highly activated species. Susceptible groups, such as isocyanates, esters, anhydrides, epoxides and the like are largely decomposed. Thus, the polymers deposited onto the substrate represent complex, rather undefined structures formed by a multitude of recombination processes among the variety of fragments. As a result, functional coatings made by "in-glow" plasma polymerization usually exhibit a larger variety of O- and N-containing reactive groups. Moreover electrons and high energy photons derived from the aforesaid processes can further affect the structure and the composition of the coatings. These coatings do not possess a highly regular arrangement of unaltered monomer residues which is desirable in view of the permeability characteristics required in case of coatings for biomedical devices like contact lenses. A further problem encountered with the in-glow plasma polymerization process is that the deposition of the coating is usually accompanied by a simultaneous competitive surface erosion process caused by the bombardment by the highly activated molecule fragments. As a result of the primary and secondary reactions such plasma coatings usually are heavily restricted in their permeability behaviour due to high cross-linking.

Modifications of the "in-glow" plasma polymerization process are "post-plasma" poly-merization or -coating or -deposition which is also called "plasma-induced" polymerization or -coating or -deposition, and "after-glow" plasma-induced polymerization or -coating or -deposition which is also called "downstream" plasma-induced polymerization or -coating or -deposition, or "remote" plasma-induced polymerization or -coating or -deposition.

For "post-plasma" polymerization the surface of a substrate is treated first with a non-polymerizable plasma gas (e.g. $H_2$, He or Ar) and then in a subsequent step the surface thus activated is exposed to a monomer with the plasma power having been switched off. The activation results in the plasma-induced formation of radicals on the surface which in the subsequent step initiate the polymerization of the monomer thereon.

While post-plasma polymerization is a process in which the monomer to be polymerized is not exposed to the high energy plasma and is thus not suffering activation and/or fragmentation, the method is of limited use because of the low deposition rates.

In contrast to the post-plasma polymerisation process in which polymerization is carried out on the activated substrate after the plasma power has been switched off "afterglow" plasma-induced polymerization is a process in which polymerization is effected in the presence of the plasma but wherein the substrate as well as the inlet for the monomer feed are located outside of (below) the plasma zone. Fragmentation of the monomer molecules can be largely avoided in this way as the monomer does not pass the zone of the highly reactive plasma gases. With this process the structure of the polymer deposit can be controlled within certain limits, undesired surface erosion of susceptible substrates can be avoided and the formation of the polymer deposit is predominantly based on radical reactions.

It is an object of the present invention to provide articles having a polymeric primary coating which exhibits excellent adherence to the substrate and contains a rather high content of reactive groups, which groups are capable of undergoing fast and efficient addition reactions even in aqueous environments and which are obtained by plasma-induced polymerization of a polymerizable unsaturated compound carrying said reactive groups. If desired, the polymerizable unsaturated compound carrying said reactive group might be blended with one or more non-reactive polymerizable unsaturated compounds or with unsaturated compounds carrying another type of functionality. Such blends might typically contain up to 60 weight %, preferably up to 20 wt. % and more preferably up to 10 wt. % of non-reactive polymerizable usaturated compounds, but unblended are most preferred. The polymer chains of the coating while exhibiting controlled crosslinking are composed to a large extent of repeating units which are identical in structure to the repeating units obtained by non-plasma radical polymerization of the said polymerizable unsaturated compound.

The term "reactive groups" denotes within the present invention an isocyanato, isothiocyanato, epoxy, anhydride, azlactone or a lactone group, which is capable of undergoing typically an addition reaction, with a monomeric, oligomeric or macromolecular compound of synthetic, semisynthetic or biological origin, to form the final coating. A highly preferred reactive group is the isocyanato group.

It is a further object of the present invention to provide primary coatings of the above mentioned type which may be applied to a wide variety of substrates including organic polymers and inorganic materials such as metals, metal oxides, ceramic materials, glass, minerals and carbon including graphite, or composites of these materials. Prior to said coating, said materials might be molded or shaped in many different ways, for example as nano- or microparticles, fibres, films, membranes, (micro)capsules, granules, (micro)beads, rods, sheets, hollow fibres, tubules, pipes, electrodes, (micro)chips, optical fibres, wave guides, valves and the like.

Another object of the invention is to provide primary and secondary coatings to porous substrates without destroying their permeation characteristics.

It is a more specific object of the invention to provide primary and secondary coatings of the above-mentioned type on a biomedical material or article, especially an ophthalmic implant or a contact lens, most specifically an artificial cornea, an intraocular lens or an extended wear contact lens which coating excels by good adherence to the substrate and superior biocompatibility, exhibits good permeability for oxygen, carbon dioxide, proteins, lipids, water and ions, high wettability, wear resistance, stability towards tear liquid and deposition of proteins, lipids, mucins and salts and shows excellent comfort for the wearer on continuous wearing, preferably of more than 6 days and 6 nights.

It is a further object of the invention to provide a method for preparing articles having a primary polymeric coating which exhibits excellent adherence to the substrate, has a structure of the repeating units as mentioned above and carries reactive groups on the surface in a simple and reliable one-step-process.

It is a further object to provide articles having a hybrid-type coating obtainable by reacting the reactive groups comprised in the primary coating with a monomeric, oligomeric or macromolecular compound of synthetic, semisynthetic or biological origin. Said hybrid-type coatings exhibit outstanding thermal, oxidative and hydrolytic stability and resistance to delamination from the substrate caused by mechanical stress, desirable permeation characteristics for liquids, gases, ions, nutrients and low molecular weight compounds while having controlled permeability for high molecular weight biocomponents, such as proteins, glycoproteins and lipids.

The term "hybrid-type coating" relates within the terms of the present invention to a primary coating with the provisio that the reactive groups have been modified to an unreactive moiety. In more detail, the hybrid-type coating might either represent a real layer by layer coating or it might represent a primary coating with an additional monomolecular layer only. Accordingly, this modification might be either effected with the above mentioned monomeric, oligomeric or macromolecular compound of synthetic, semisynthetic or biological origin, or it might be effected by any addition reaction of substanatially any suitable molecule, such as addition of water, ammonia, $C_1$–$C_7$ alkanol, e.g. methanol, $C_1$–$C_7$ aminoalkane, e.g. methylamine, propylene glycol, glycerol, amino acid, carbohydrate or the like.

Another more specific object of the invention is the provision of a biomedical material or article as mentioned above having a hybrid-type coating as mentioned in the preceding paragraph which also has excellent wettability by aqueous solutions such as tear fluid, and provides for example on a contact lens a tear film break up time of >10 seconds.

Another object is an article, in particular a biomedical or bioanalytical device having a hybrid-type coating as mentioned, which provides specific (bio)affinity or (bio)activity properties to the device. Examples of biomaterials forming the outer layer of the hybrid-type coating, obtained by reacting with the reactive primary coating are:

Carbohydrates, oligosaccharides, polysaccharides, sugars, cyclodextrins, heparin, dextrans and glycoaminoglycans;

Peptides or proteins such as cell adhesion and antiadhesion factors, cell growth factors, enzymes, coenzymes, receptor proteins, lectins, antibodies, antigenes;

Glycopeptides, glycoproteins and lipoproteins, such as mucins and immunoglobulins;

Phospholipids, glycolipids and lipoproteins, such as sphingolipids;

Nucleotides; such as DNA- or RNA-oligonucleotides;

Affinity species, which are capable of attracting, assembling and/or temporarily binding specific molecular species, e.g. through a lock/key, host/guest and otherwise complementary interaction or complex formation (examples of such molecular species are biotin/avidin, cyclodextrin/host, antibody/antigen, enzyme/substrate/inhibitor, DNA/DNA, DNA/RNA, lectin/carbohydrate, drug/receptor protein etc.); and Any of the above mentioned biomaterials which carries a specific label like a fluorescent dye (FITC), colloidal gold, radio lablels, peroxidase and the like, thus making the coated surface suitable for analytical and diagnostic techniques.

The invention also relates to a device which contains an article coated according to the above described technology. Examples of such a device are an ophthalmic device such as a contact lens, an intraocular lens or an artificial cornea; an artificial organ such as liver, pancreas, kidney or heart; drug delivery systems such as (micro)capsules, (micro)beads and transdermal membranes or a drug targeting system such as tumor targeting or brain targeting; a bioanalytical system, affinity carrier or a permselective membrane; prostheses and surgical repair or implant materials and devices such as vascular grafts, bone repairs, nerve repairs, dental repairs or catheters.

These objects could be achieved on the basis of the finding, that primary coatings having a variety of desirable characteristics as mentioned above can be produced by plasma-induced polymerization of a polymerizable unsaturated compound carrying reactive groups on a substrate in the after-glow zone of a plasma apparatus under specifically controlled conditions including the distance of substrate and monomer inlet to the plasma zone.

Within the terms of the present invention, a polymerizable unsaturated compound carrying reactive groups is understood to represent a monomer, a comonomer, a polymer or a copolymer, which carries an unsaturated moiety such as vinyl or isopropenyl as well as a reactive group.

A subject matter of the present invention is thus an article comprising a substrate with a primary polymeric coating carrying reactive groups predominantly on its surface, wherein said polymeric coating comprises repeating units derived from a polymerizable unsaturated compound carrying reactive groups, wherein in said coating the concentration of said reactive groups is, based on spin label determination by ESR spectroscopy, in a range of $0.2$–$20 \cdot 10^{-9}$ Mol spin/cm$^2$, preferably in a range of $0.5$–$15 \cdot 10^{-9}$ Mol spin/cm$^2$ and more preferably in a range of $2$–$12 \cdot 10^{-9}$ Mol spin/cm$^2$.

A preferred aspect of the invention relates to articles, wherein said primary polymeric coating might additionally comprise repeating units derived from one or more polymerizable unsaturated compounds not carrying reactive groups.

Another preferred aspect of the invention relates to articles, wherein said primary polymeric coating comprises repeating units derived from one or more polymerizable unsaturated compounds carrying reactive groups.

In a further preferred aspect, the invention relates to articles, wherein 30% to 98%, preferably 50%–90% and more preferably 60% –80% of the repeating units are identical in structure to those repeating units obtained by non-plasma radical polymerization of said unsaturated compounds and wherein 2% to 70%, preferably 10% to 50% and more preferably 20 to 40% of the repeating units represent sites of cross-linkage and/or covalent bonding to the substrate.

Typically, a primary coating according to the present invention exhibits a thickness of about $0.001$–$10\ \mu m$. A spin label determination experiment by ESR typically pertains to the three-dimensional concentration of reactive groups, for example reactive groups per cubic centimeter (cm$^3$). Consequently, the concentration of reactive groups, as determined by ESR, reflects the total amount of such groups for a volume underlying an area of e.g. one square centimeter (1 cm$^2$). For very thin coatings, this volume corresponds almost to the two-dimensional area. Consequently, for very thin primary coatings, the concentration of reactive groups approximately reflects the concentration of reactive groups on the surface. For instance, in primary coatings having a thickness of 1–10 nm, the number of reactive groups is typically in the order of 0.01 to 5 reactive groups per square nanometer, and is typically depending on the nature of the monomers used.

The term primary coating relates to a polymeric coating comprising reactive groups.

The thickness of such a primary coating is typically in the range of $0.001$–$10\ \mu m$, preferably in the range of $0.01$–$1\ \mu m$ and more preferably in the range of $0.03$–$0.2\ \mu m$.

According to the invention the adherence of the coating to the substrate and the degree of crosslinking of the polymeric coating are such that the hybrid-type coating obtained after reaction of the reactive groups with a suitable monomeric, oligomeric or macromolecular compound of synthetic, semisynthetic or biological origin, shows thermal, oxidative and hydrolytic stability and resistance to delamination caused by mechanical stress and that said coating is permeable to gases, water, nutrients and ions having a molecular weight below 500 and has a controlled permeability for biocomponents, such as proteins, glycoproteins and lipids.

In a specifically preferred aspect of the present invention the substrate which is at least partially coated with a polymer as indicated above (secondary coating) is a biomedical material, article, or device including catheters and vascular grafts, especially an ophthalmic device for vision correction, such as a contact lens, an intraocular lens, or an extended wear contact lens and most specifically a lenticular corneal onlay or implant.

According to another embodiment of the present invention the degree of crosslinking of the primary polymer coating carrying reactive groups may be further controlled by adding at least one crosslinking agent to the monomer feed which is subjected to after-glow plasma-induced polymerization.

According to a specific embodiment of the present invention a multilayer primary coating having "tailored" permeability performance as well as defined structure and morphology can be prepared by after-glow plasma-induced polymerization according to the present invention, if at first one or more polymerizable unsaturated compounds without reactive groups, and then a polymerizable unsaturated compound carrying reactive groups, each one optionally together with crosslinking agents and/or polymerizable unsaturated compounds without reactive groups, are subjected to polymerization one after the other, preferably without interrupting the glow discharge.

A further subject matter of the present invention is a method for preparing an article as indicated above which comprises carrying out after-glow plasma-induced polymerization of a polymerizable unsaturated compound carrying reactive groups on a substrate wherein the substrate is positioned at a distance of 4 to 40 cm and the monomer inlet at a distance of 3 to 35 cm downstream outside the plasma zone.

Within the terms of the present invention, the plasma generation may be generated by any means such as RF (radiofrequency), MW (microwave) or DC (direct current) technique. The sample temperature in the plasma reactor is typically in a range of 0–100° C., preferably in a range of 80–10° C., more preferably in a range of 80–50° C. and very preferably in a range of 40–20° C.

After-glow plasma induced polymerization of a polymerizable unsaturated compound carrying reactive groups in accordance with the invention is typically carried out under the following plasma conditions:

| | |
|---|---|
| Electric power | 40–300 watts, upper range up to 600 watts, applied power is dependent upon reactive group (see examples) |
| Electric voltage | $8 \cdot 10^2 - 4 \cdot 10^3$ volts |
| Plasma gas flow | 1–100 (standard cubic centimeter) sccm |
| Monomer flow | 1–50 mg/min |
| Feed gas flow | 1–100 (sccm) |
| Temp. of the monomer source | −80° C. – +80° C. |
| Frequency | 1 kHz – 27.12 MHz, most preferably 13.56 or 27.12 MHz |
| Plasma gases | Ar, He, $N_2$ |
| Pressure | $1 \cdot 10^{-4} - 5$ mbar, |

Throughout the present invention, the term monomer or comonomer is used equivalently to the expression, polymerizable unsaturated compound.

The substrate distance downstream from the plasma zone is preferably 8–30 cm, most preferably 10–25 cm. The monomer inlet distance downstream from the plasma zone is preferably 6–25 cm, most preferably 8–20 cm. Preferably an inductively-coupled, pulsed radio frequency glow discharge plasma is used.

A further subject-matter of the present invention is an article having a hybrid-type coating obtainable by reaction of the article having a polymeric coating carrying reactive groups on the surface with a suitable monomeric, oligomeric or macromolecular compound of synthetic, semisynthetic or biological origin.

The polymeric coatings of the present invention carrying reactive groups which are obtainable by after-glow plasma-induced polymerization of a polymerizable unsaturated compound on a substrate under the conditions mentioned regarding the distance between substrate and plasma zone as well as monomer inlet and plasma zone are characterized—contrary to coatings obtained by in-glow plasma-induced polymerization or by after-glow plasma-induced polymerization without observing these conditions—by the fact that the repeating units of the polymer chains are to a large extent identical in structure to those repeating units obtained through a non-plasma radical polymerization of the respective unsaturated compound.

The uniform structure and the controllable relatively low degree of crosslinking of the coatings which is surprisingly achieved in the after-glow or downstream embodiment of the plasma-induced polymerization of a polymerizable unsaturated compound under the relatively mild plasma conditions and the specific conditions of the position of substrate and monomer inlet constitutes a characteristic feature of the coatings which is responsible for a wide variety of advantageous properties exhibited by these coatings, especially in view of their use in biological systems including biomedical applications, articles or devices.

A specific advantage of the coatings is their strong adherence to the surface of the coated substrate which is obtained to a large degree independently from the nature of the substrate, whether it is a polymeric organic material or an inorganic material such as a metal, metal oxide, ceramic material, glass or a mineral or carbon, especially graphite or glassy carbon. Also composite materials including two or more of the above mentioned substrate materials may be coated with a primary and/or secondary coating of the invention.

A further specific advantage of the primary polymeric coatings is the fact that they exhibit a high density of reactive groups on their surface providing a high number of linkage sites for the secondary coating reaction with a suitable monomeric, oligomeric or macromolecular compound of synthetic, semisynthetic or biological origin. The final product, which results thereof, has a number of technically and biologically advantageous properties including high wettability and biocompatibility. This advantage follows from the unexpected finding that the reactive groups of the polymerizable unsaturated monomer remain unaltered to a large extent during after-glow plasma-induced polymerization while they are decomposed almost entirely in in-glow plasma-induced polymerization and other plasma conditions described above, so that only very low surface functionality can be achieved.

The high degree of structural uniformity of the polymer chains, the low degree of crosslinking and the predominantly brush-type structure of the coatings of the invention carrying reactive groups on the surface to the substrate provide the article having the final coating (primary coating reacted with a monomeric, oligomeric or macromolecular compound of synthetic, semisynthetic or biological origin) of the invention with superior characteristics (according to the nature of the final coating) for a wide variety of applications including:

excellent adherence to the substrate and wear resistance;

excellent thermal, oxidative and hydrolytic stability and resistance to delamination caused by mechanical stress;

good permeation characteristics for liquids, gases, ions, nutrients and low molecular weight compounds;

controlled permeability for biocomponents, such as proteins, glycoproteins and lipids;

high resistance against temperature changes, autoclaving, bioerosion, swelling and shear forces;

smooth surface down to the sub-micron area, uniform layer thickness and excellent lubrication properties;

high resistance and durability in biological surroundings, good resistance against formation of irreversible deposits of components from biological systems, such as proteins, lipids, glycoproteins, salts and metabolites and cell debris;

low tendency for absorption of substances from the surroundings, such as cosmetics, solvent vapors and dusts;

no tendency for adherence of microorganisms.

The extraordinary features of the primary as well of the final, hybrid-type coating with regard to biocompatibility, bioaffinity, bioactivity and in general to resistance against formation of irreversible deposits as well as to permeability are due to the fact that polymer chains within the coating still possess pronounced dynamics and mobility. In biological surroundings, secondary (or hybrid-type) coatings show in general a substantially reduced tendency to cause denaturation of biocomponents. Moreover, through proper choice of the constituents of the final coating the bioadhesion properties of a biomechanical device or of a membrane can be varied within wide ranges. The coatings can thus provide a substrate with such contradictory effects as improved cell attachement and tissue integration for artificial organ applications and anti-biofouling for membrane systems.

As mentioned above, there is substantially no limitation with respect to the form of the substrate to be coated for preparation of an article according to the invention, as long as it can be brought into and held in the after-glow zone of a plasma generating device. Specific examples of forms of substrates which may be coated according to the invention include films, fibers, membranes, sheets, hoses, tubes, hollow fibers, capsules, beads and granules of different size including powder type materials as well as composites and laminates. A specific group of substrates which is envisaged within this invention are biomedical materials or articles, especially ophthalmic devices for vision correction. These include lenticular corneal implants (artificial cornea), contact lenses and intraocular lenses.

The substrate includes e.g. any material conventionally used for the manufacture of biomedical devices, e.g. contact lenses, which are not sufficiently hydrophilic and/or biocompatible per se. Such materials are known to the person skilled in the art and may comprise for example polysiloxanes, fluorinated (meth)acrylates or equivalent fluorinated comonomers derived e.g. from other polymerizable carboxylic acids, alkyl (meth)acrylates or equivalent alkyl comonomers derived from other polymerizable carboxylic acids, or fluorinated polyolefins, such as fluorinated ethylene or propylene polymers and copolymers, or tetrafluoroethylene, preferably in combination with specific dioxols, such as perfluoro-2,2-dimethyl-1,3-dioxol.

The substrate also includes any material conventionally used for the manufacture of biomedical devices, e.g. contact lenses, which are hydrophilic per se, since functional groups, e.g. amine or hydroxy groups are inherently present in the material and therefore also at the surface of a biomedical device manufactured therefrom. In this case a specific interphase layer between the substrate and the primary coating can be formed through reaction of the functional groups of the substrate and the coating. Such materials are known to the person skilled in the art. Typical examples comprise e.g. Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon or Atlafilcon. Most of these materials are HEMA and or NVP based, but suitable materials may also be based on other underlying monomers or polymers having reactive groups, e.g. hydroxy groups or amino groups, such as e.g. polyvinyl alcohol.

A polymer substrate, in particular a polymer which is suitable as an artificial cornea, e.g. a corneal onlay, might be coated, preferably on its its outer (front) surface, with a hybrid-type coating according to the present invention. Such a hybrid-type coating promotes typically a selective growth of tissue (e.g. corneal epithelial cells) on said outer surface. Typical secondary coating materials of such hybrid-type coatings are peptides, proteins, glycoproteins, carbohydrates, polysacharides such as collagen, laminin, albumin, extracellular matrix proteins, cell adhesion proteins, growth factors, fibronectin, vitronectin, chondronectin, fibrin, globulins, muscle fibre proteins, vitrogen, genetically engineered peptides and proteins, lectins, hirudin, mucin, chondroitin sulfate, aminodextran, hyaluronic acid, sialic acid, L-fucose, N-acetyl galactosamin and/or derivatives, active fragments and mixtures thereof. Fibronectin, collagen, epidermal growth factors and/or derivatives, active fragments and mixtures thereof are particularly useful. A surface coating of this type can typically exhibit a plurality of advantageous properties, for example the attachment of cells with good biostability and resistance to deposits.

The inner (back) surface of an artificial cornea, e.g. a corneal onlay lenticule might be coated with another coating (relative to the front surface), e.g. as follows:

(a) Either with a primary coating carrying reactive groups according to the present invention, such as OCN— or epoxy groups, for the firm binding of the onlay to the underlying material of the corneal Basement Membrane or Bowman's Membrane through chemical reaction, or;

(b) With a secondary hybrid-type coating according to the present invention, which mediates strong affinity of the onlay to the underlying material of the Basement Membrane or Bowman's Membrane and in a specific embodiment of the invention prevents corneal epithelial cell attachment and growth on this back surface.

In case of an artificial cornea device designed for implantation into the corneal stroma (corneal inlay) both surfaces can be coated according to the present invention with a hybrid-type coating, which provides good long-term biocompatibility and tissue integration to the implant.

The polymer substrate may be any blood-contacting material conventionally used for the manufacture of renal dialysis membranes, blood storage bags, pacemaker leads or vascular grafts. For example, the substrate may be a polyurethane, polydimethylsiloxane, polytetrafluoroethylene, perfluoroalkyl-polyether, polyvinylchloride or Dacron™.

In a specifically preferred embodiment of the present invention the substrate to be coated (with a secondary coating) is a contact lens suitable for extended wear, i.e. for continuous wear of more than six days and six nights up to a time of about 30 days. This type of soft contact lenses includes those comprising polysiloxane and/or perfluoroalkyl-polyether groups which exhibit the desired high oxygen- as well as high ion- and water-permeability. If this type of substrate is coated in accordance with the present invention with a hydrophilic compound, coated contact lenses are obtained which exhibit the following desirable properties as compared to conventionally surface coated contact lenses:

increased permeability for oxygen, carbon dioxide, water and ions;

excellent wettability, lubricity and stability in the ocular liquid surroundings;

improved comfort for the wearer as well as resistance against irreversible deposition on the surface of the lens of substances occurring in the ocular surroundings, including proteins, lipids, mucins and salts;

decreased adhesiveness for microorganisms;

decreased tendency of microcrack formation within the coating during sterilization in the autoclave in phosphate buffered saline;

superior on-eye performance including very low cornea swelling, eye irritation and very good lens mobility on the eye during continuous wear of the lens over an extended time of up to 30 days.

In the case of implants a secondary coating in accordance with the present invention prepared from a suitable biomaterial or a hydrophilic synthetic compound provides articles having surface and permeability characteristics including an open, only slightly cross-linked polymer structure which exhibits excellent biocompatibility and leads to firm cell adhesion and to good and durable integration into the living tissue.

The monomer which may be used to prepare the primary coating carrying reactive groups by after-glow plasma-induced polymerization may be any polymerizable unsaturated compound which carries reactive groups and can be evaporated and introduced into the after-glow zone of a plasma generating apparatus to contact the substrate provided therein.

Examples of reactive groups to be contemplated herein include isocyanate (—NCO), isothiocyanate (—NCS), epoxy, anhydride, azlactone and lactone (e.g. $\beta$-, $\gamma$-, $\delta$-lactone) groups.

An azlactone is particularly preferred, since it exhibits a higher selectivity, in particular when the primary reactive plasma coating is reacted with amino-group containing compounds, e.g. with proteins in aqueous solutions. The stability in such aqueous solutions at room temperature is higher too.

Specific examples of preferred polymerizable unsaturated compounds carrying reactive groups are 2-isocyanatoethyl-methacrylate (IEM), glycidyl methacrylate, (meth)acrylic acid anhydride and 4-vinyl-2,2-dimethylazlactone.

The article having a primary polymeric coating carrying reactive groups which constitutes one subject-matter of the invention is a kind of intermediate product which is reacted with a monomeric, oligomeric or macromolecular compound of synthetic, semisynthetic or biological origin providing desirable surface properties including wettability to the final laminate coated product. Specific examples of a monomeric, oligomeric or macromolecular compound of synthetic, semisynthetic or biological origin envisaged as top coatings which may be used for modifying the reactive surface are proteins, such as albumin, hirudin and lectins; glycoproteins, such as mucin; carbohydrates, such as cyclodextrines or 8-aminooctyl-lactobionoamide; polysaccharides, such as chitosan; and amino functionalized polymers and telomers such as Jeffamines and polyvinylalcohol (PVA), poly-N-vinyl pyrrolidone (poly-NVP), polyethylene glycol (PEG) and poly-acrylamide.

The primary polymeric coatings carrying reactive groups are prepared on at least a part of the surface of a substrate to give a coated article having a reactive surface by plasma-induced polymerization of a polymerizable unsaturated compound in the after-glow or downstream area of a plasma reactor. The process parameter including the physical plasma parameters of the deposition process are controlled in such a way that the desired amount of repeating units which are identical in structure to those repeating units obtained by non-plasma radical polymerization of the polymerizable unsaturated compound, the desired degree of crosslinking and the desired morphology and topography are obtained on the specific substrate. These parameters and characteristics as well as the thickness of the coating may be tailored within broad ranges by suitably selecting the plasma and reaction parameters. Compared to other coating processes the method of preparing polymeric coatings carrying reactive groups according to the invention offers the following advantages (e.g. for coating contact lenses):

the coated substrates are obtained under sterile conditions;

very low surface erosion and high deposition rate;

smooth, pinhole-free coatings are obtained;

the thickness of the coating can easily be controlled up to relatively thick coatings of more than 1 $\mu$m;

low content of radicals remaining in the coating;

no uncontrolled secondary reactions with air to hydroperoxides and other reactive species;

excellent thermal and hydrolytic stability of the coatings which do not contain leachable parts;

high UV and light stability of the coatings;

uniform layer thickness on non-flat substrates including good edge coating;

homogenous surface groups;

high content of "brush-type" surface structures with low tendency for denaturation of biopolymers or other biocomponents and irreversible adsorption (biofouling);

no fragmentation of the monomers employed and no bombardment of the surface of the substrate by atoms, ions, excited species or high energy UV-radiation during the coating process leading to undesired secondary changes of the coating and/or the substrate and to detrimental surface erosion.

no tendency to delamination of the coatings on thermal, hydrothermal and mechanical stress.

The articles of the present invention having a hybrid-type (secondary)coating obtainable by reaction of the reactive groups present on the (primary) coating obtained by after glow plasma-induced polymerization with a suitable monomeric, oligomeric or macromolecular compound of synthetic, semisynthetic or biological origin exhibit bioactive, biocompatible and wettable coatings on a wide variety of biomaterials including artificial cornea and contact lenses and impart specific (bio)affinity or (bio)activity properties to such a device. As mentioned before, catalysts, enzymes, antibodies and similar materials may also be immobilized by reaction with the reactive groups present on the said primary polymeric coating.

As mentioned before, the reactive groups of the primary coating may be modified with substantially any suitable molecule or compound which is capable of forming an addition reaction with a corresponding reactive group. Examples of suitable molecules or compounds range from small molecules such as ammonia, water, alcohol to highly complex compounds such as enzymes, glycoproteins or nucleotides. Further specific examples are listed above.

The reactive groups may be modified by these compounds in solution or in pure form. If pure and if appropriate, they may be applied as a gas or a liquid. Solvents suitable for solutions should be substantially inert to the reactive groups or should at least exhibit a clearly attenuated reactivity in comparison to the reactivity of the compound to be added. Suitable examples thereof are ethers, such as tetrahydrofuran (THF), diethyl ether, diethylene glycol dimethyl ether or dioxane, halogenated hydrocarbons, such as chloroform or methylene chloride, bipolar aprotic solvents, such as acetonitrile, acetone, dimethylformamide (DMF) or dimethyl sulfoxide (DMSO), hydrocarbons, such as hexane, petroleum ether, toluene or xylene, and furthermore pyridine or N-methylmorpholine.

The temperatures used in an above secondary modification reaction range typically from −20° C. to 150° C., preferably from 0–100° C. and in particular from 20–60° C. The reaction time ranges typically from a few seconds to several days, preferably from about 30 seconds to 24 hours and more preferably from 1 minute to 12 hours.

The reaction of a reactive group with a molecule or a compound may be monitored with several analytical methods such as spectroscopy. Specific methods thereof are Fourier Transformation Infrared—Attenuated Total Reflection Spectroscopy (FTIR-ATR), ESCA, Electron Spin Resonace (ESR) and TOF-SIMS.

An above molecule or compound may either be used separately or in mixtures. It is not a prerequisite that in such a mixture the compounds or molecules present exhibit comparable reactivities. To the contrary, such might be used for limiting the quantity of a certain species on a coating surface. If appropriate, said final coating may be carried out in several steps sequentially. Another method for limiting the amount of a species on a final coating is for example the addition of a highly reactive gas, which would immediately quench the addition reaction when needed.

A third possibility for graded surface loading exists in using mixtures of polymerizable unsaturated compounds carrying reactive groups and polymerizable unsaturated compounds carrying no reactive groups for the primary plasma-induced polymerization thus generating primary surfaces of graded functionality. Typically, the relative amount of polymerizable unsaturated compounds carrying reactive groups ranges in wt. % from 100%–10%, preferably from 80%–50%, and more preferably from 70%–40%; the remainder to 100 wt. % being a polymerizable unsaturated compound carrying no reactive group.

The thickness of a final polymeric hydrid-type coating is typically in the range of 1 to 5'000 nm, preferably in the range of 5 to 1'000 and in particular from 10 to 500 nm.

As already mentioned above, in an important aspect, the present invention refers to contact lenses comprising a final coating according to the invention on a suitable lens body which—because of the outstanding properties of the coating including high oxygen transmissibility, high permeability for ions and water and good movement on the eye—may be used for extended periods of wear, e.g., up to 30 days. Important characteristics of such contact lenses and methods for their determination will be explained infra. Many of these aspects are important for artificial cornea as well. In addition, artificial cornea applications require protein permeability.

Oxygen Transmibility and Permeability

The "oxygen transmissibility of a lens, as used herein, is the rate at which oxygen will pass through a specific ophthalmic lens. Oxygen transmissibility, $D_k/t$, is conventionally expressed in units of barrers/mm, where t is the average thickness of the material [in units of mm] over the area being measured and "barrer" is defined as:

$$[(cm^3 \text{ oxygen}) (mm)/(cm^2) (sec) (mm Hg)] \cdot 10^{-9}$$

The "oxygen permeability", $D_k$, of a lens material does not depend on lens thickness. Oxygen permeability is the rate at which oxygen will pass through a material. Oxygen permeability is conventionally expressed in units of barrers, where "barrer" is defined as:

$$[(cm^3 \text{ oxygen}) (mm)/(cm^2) (sec) (mm Hg)] \cdot 10^{-10}$$

These are the units commonly used in the art. Thus, in order to be consistent with the use in the art, the unit "barrer"

will have the meanings as defined above. For example, a lens having a $D_k$ Of 90 barrers ("oxygen permeability barrer") and a thickness of 90 microns (0.090 mm) would have a Dk/t of 100 barrers/mm ("oxygen transmissibility barrers"/mm).

The oxygen transmissibility of the extended-wear lens from the outer surface to the inner surface must be sufficient to prevent any substantial corneal swelling during the period of extended wear. It is known that the cornea swells approximately 3% to 4% during overnight periods of sleep when the eyelids are closed, as a result of oxygen deprivation. It is also known that wearing a conventional contact lens for a period of about 8 hours (overnight wear) causes corneal swelling of about 11%. However, an acceptable extended-wear contact lens will produce, after wear of about 24 hours, including normal sleep periods, corneal swelling of less than about 8%, more preferably less than about 6%, and most preferably less than about 4%. A preferred extended-wear contact lens will produce, after wear of about 7 days, including normal sleep periods, corneal swelling of less than about 10%, more preferably, less than about 7%, and most preferably less than about 5%. Thus, the extended wear lens must have oxyperm polymer in an amount sufficient to produce oxygen diffusion to yield the above properties relating to corneal swelling. Preferably, the extended-wear lens has a continuous phase of oxyperm polymer extending from the outer surface to the inner surface of the lens.

The oxygen permeability of a lens and oxygen transmissibility of a lens material may be determined by the following technique. Oxygen fluxes (J) are measured at 34° C. in a wet cell (i.e., gas streams are maintained at about 100% relative humidity) using a Dk1000 t:-4 instrument (available from Applied Design and Development Co., Norcross, Ga.), or similar analytical instrument. An air stream, having a known percentage of oxygen (e.g., 21%), is passed across one side of the lens at a rate of about 10 to 20 cm³/min., while a nitrogen stream is passed on the opposite side of the lens at a rate of about 10 to 20 cm³/min. The barometric pressure surrounding the system, $P_{measured}$, is measured. The thickness (t) of the lens in the area being exposed for testing is determined by measuring about 10 location with a Mitotoya micrometer VL-50, or similar instrument, and averaging the measurements. The oxygen concentration in the nitrogen stream (i.e., oxygen which diffuses through the lens) is measured using the DK1000 instrument. The oxygen permeability of the lens material, $D_k$, is determined from the following formula:

$$D_k = Jt(P_{oxygen})$$

where

J=oxygen flux [microliters$_{O2}$/cm²-minute]

$P_{oxygen}$
  =($P_{measured}$–$P_{water\ vapor}$)·(% $O_2$ in air stream) [mm Hg]
  =partial pressure of oxygen in the air stream $P_{measured}$=barometric pressure [mm Hg]

$P_{water\ vapor}$=0 mm Hg at 34° C. (in a dry cell) [mm Hg]

$P_{water\ vapor}$=40 mm Hg at 34° C. (in a wet cell) [mm Hg]

t=average thickness of the lens over the exposed test area [mm]

where $D_k$ is expressed in units of barrers, i.e., [(cc oxygen)(mm)/cm²]·[sec/mm Hg]·10$^{-10}$.

The oxygen transmissibility ($D_k/t$) of the material may be calculated by dividing the oxygen permeability ($D_k$) by the average thickness (t) of the lens.

The oxygen transmissibility ($D_k/t$) of the extended-wear lens of the invention is preferably at least 70 barrers/mm, more preferably at least 75 barrers/mm, and most preferably at least 87 barrers/mm. The lens center thickness is typically more than about 30 microns, preferably about 30 to about 200 microns, more preferably about 40 to about 150 microns, even more preferably about 50 to about 120 microns, and most preferably about 60 to 100 microns.

Ionoflux Measurement Technique

The following technique, referred to herein as the "Ionoflux Technique", is a preferred method for determining the ion permeability of a lens. This technique may be used to determine the likelihood of adequate on-eye movement.

The "Ionoflux Technique" involves the use of a conductometer (LF 2000/C, catalog, no. 300105, Wissenschaftlich-Technische Werkstätten GmbH (WTW), Germany), an electrode equipped with a temperature sensor (LR 01/T, catalog no. 302 520, (WTW)), a donor chamber containing a salt solution, a receiving chamber containing about 60 ml of deionized water, a stir bar and a thermostat.

The donor chamber is specially designed for sealing a contact lens thereto, so that the donor solution does not pass around the lens (i.e., ions may only pass through the lens). The donor chamber is composed of a glass tube which is threaded at the end which is immersed in the receiving solution. The glass tube includes a centrally located hole of about 9 mm in diameter. A lid, which is threaded to mate with the glass tube, holds a lens-retaining member which includes a centrally located hole of about 8 mm in diameter. The lens-retaining member includes a male portion adapted to mate with and seal the edges of the inner (concave) surface of a lens and a female portion adapted to mate with and seal the edges of the outer (convex) surface of a lens.

The lens to be measured is placed in the lens-retaining device, between the male and female portions. The male and female portions include flexible sealing rings which are positioned between the lens and the respective male or female portion. After positioning the lens in the lensretaining device, the lens-retaining device is placed in the threaded lid. The lid is screwed onto the glass tube to define the donor chamber. The donor chamber is filled with 16 ml of 0.1 molar NaCl solution. The receiving chamber is filled with 60 ml of deionized water. The leads of the conductivity meter are immersed in the deionized water of the receiving chamber and a stir bar is added to the receiving chamber. The receiving chamber is placed in a thermostat and the temperature is held at about 35° C. Finally, the donor chamber is immersed in the receiving chamber.

Measurements of conductivity are taken every 20 minutes for about three hours, starting 10 minutes after immersion of the donor chamber into the receiving chamber. The Ionoflux Diffusion Coefficient, D, is determined by applying Fick's law as follows:

$$D = -n'/(A \cdot dc/dx)$$

where n'=rate of ion transport [mol/min]

A=area of lens exposed [mm²]

D=Ionoflux Diffusion Coefficient [mm²/min]

dc=concentration difference [mol/L]

dx=thickness of lens [mm]

An Ionoflux Diffusion Coefficient of greater than about $6.4 \cdot 10^{-6}$ mm²/min is preferred for achieving sufficient on-eye movement. More preferably, the Ionoflux Diffusion Coefficient is greater than about $2.6 \cdot 10^{-6}$ mm²/min, while most preferably the Ionoflux Diffusion Coefficient is greater than about $1.5 \cdot 10^{-5}$ mm²/min. It must be emphasized that the Ionoflux Diffusion Coefficient correlates with ion permeability through the lens, and thereby is a predictor of on-eye movement.

Contact Angle Measurements

Advancing and receding water contact angles of coated and non-coated lenses were determined with the dynamic Wilhelmy method using a Krüss K12 instrument (Krüss GmbH, Hamburg). For details it is referred to D. A. Brandreth: "Dynamic contact angles and contact angle hysteresis", Journal of Colloid and Interface Science, vol. 62, 1977, pp. 205–212 and R. Knapikowski, M. Kudra: Kontaktwinkelmessungen nach dem Wilhelmy-Prinzip-Ein statistischer Ansatz zur Fehierbeurteilung", Chem. Technik, vol. 45, 1993, pp. 179–185.

Concentration of Functional Groups Generated on a Substrate Surface by After-glow Plasma Induced Polymerization of Unsaturated Reactive Monomers (1) Through reaction of the functional groups within the primary plasma coating with a solution of the spin label 4-amino-2,2,6,6-tetramethyl-piperidine-1-oxyl (4-amino-TEMPO) a quantitative conversion can be achieved. Subsequent Electron Spin Resonance (ESR) spectroscopy of the samples thus labeled leads to a highly sensitive and reliable determination of the primary functional groups. Dependant on the type of the reactive monomer and on the percentage of additional non-reactive (or unreactive) comonomers used surface functionalities ranging from $0.2–20 \cdot 10^{-9}$ Mol/cm$^2$, preferably from $0.5–15 \cdot 10^{-9}$ Mol/cm$^2$ and in particularly from $2–12 \cdot 10^{-9}$ Mol/cm$^2$ can be made.

(2) The functional surface groups can clearly be identified by Fourier Transform Infrared Attenuated Total Reflection (FTIR-ATR) Spectroscopy. The absorption bands employed for the quantification may typically be:

| isocyanate: | 2270 cm$^{-1}$, | epoxide: | 1270 cm$^{-1}$ |
|---|---|---|---|
| anhydride: | 1800, 1760 cm$^{-1}$, | azlactone: | 1820, 1770 cm$^{-1}$ |

FTIR-ATR can advantageously be used for the follow up on the consumption of functional groups during the secondary reaction with monomers, oligomers, polymers or biomaterials. Dependant on the reactivity, the molecular weight and the total functionality of the molecular species used, 60–95% conversion of the primary functional surface groups can be achieved. Typically, the residual surface functionality might subsequently be completely quenched by reaction with reactive small molecules like NH$_3$.

(3) An indirect determination of the total surface loading in monomers, oligomers, polymers or of any biomaterial obtained by secondary reaction can be accomplished by reacting the residual functionality with 4-amino-TEMPO and subsequent ESR spectroscopy. The difference between the original ESR functionality and the residual ESR functionality leads to a conclusion on the total surface loading achieved with the provision that no side reactions with solvent molecules or moisture or the like occur. The results derived from the calculation are within standard deviations (±10%) in satisfactory agreement with the conclusions drawn from FTIR-ATR measurements. Conversions of functional groups in the secondary reactions range from 60–98%.

Polymerizable unsaturated compounds carrying no reactive groups are typically hydrophobic or hydrophilic vinylic comonomers or mixtures thereof.

Suitable hydrophobic vinylic comonomers include, without this being a comprehensive list, $C_1$–$C_{18}$alkyl acrylates and methacrylates, $C_3$–$C_{18}$alkylacrylamides and -methacrylamides, acrylonitrile, methacrylonitrile, vinyl $C_1$–$C_{18}$alkanoates, $C_2$–$C_{18}$ alkenes, $C_2$–$C_{18}$ haloalkenes, styrene, $C_1$–$C_6$ alkylstyrene, vinyl alkyl ethers in which the alkyl moiety has 1 to 6 carbon atoms, $C_2$–$C_{10}$perfluoroalkyl acrylates and methacrylates and correspondingly partially fluorinated acrylates and methacrylates, $C_3$–$C_{12}$perfluoroalkyl ethylthiocarbonylaminoethyl acrylates and -methacrylates, acryloxy- and methacryloxyalkylsiloxanes, N-vinylcarbazole, $C_1$–$C_{12}$alkyl esters of maleic acid, fumaric acid, itaconic acid, mesaconic acid and the like. Preference is given to, for example, $C_1$–$C_4$alkyl esters of vinylically unsaturated carboxylic acids having 3 to 5 carbon atoms or vinyl esters of carboxylic acids having up to 5 carbon atoms.

Examples of suitable hydrophobic vinylic comonomers include methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl methacrylate, tris (trimethylsilyloxy)silylpropyl methacrylate, 3-methacryloxypropylpentamethyldisiloxane and bis(methacryloxypropyl)tetramethyldisiloxane.

Suitable hydrophilic vinylic comonomers include, without this being a comprehensive list, hydroxy-substituted lower alkyl acrylates and methacrylates, acrylamide, methacrylamide, lower alkylacrylamides and -methacrylamides, methoxylated acrylates and methacrylates, hydroxy-substituted lower alkyl-acrylamides and -methacrylamides, hydroxy-substituted lower alkyl vinyl ethers, sodium ethylenesulfonate, sodium styrenesulfonate, 2-acrylamido-2-methylpropanesulfonic acid, N-vinylpyrrole, N-vinylsuccinimide, N-vinylpyrrolidone, 2- and 4-vinylpyridine, acrylic acid, methacrylic acid, amino- (where the term "amino" also covers quaternary ammonium), mono(lower alkyl)amino- or di(lower alkyl)-amino(lower alkyl) acrylates and methacrylates allyl alcohol and the like. Preference is given to, for example, hydroxy-substituted $C_2$–$C_4$alkyl (meth)acrylates, five- to seven-membered N-vinyllactams, N,N-di-$C_1$–$C_4$alkyl(meth)acrylamides and vinylically unsaturated carboxylic acids having a total of 3 to 5 carbon atoms.

Examples of suitable hydrophilic vinylic comonomers include hydroxyethyl methacrylate, hydroxyethyl acrylate, acrylamide, methacrylamide, dimethylacrylamide, allyl alcohol, vinylpyridine, vinylpyrrolidone, glycerol methacrylate, N-(1,1-dimethyl-3-oxobutyl)acrylamide and the like.

Preferred hydrophobic vinylic comonomers are methyl methacrylate and vinyl acetate.

Preferred hydrophilic vinylic comonomers are 2-hydroxyethyl methacrylate, N-vinylpyrrolidone and acrylamide.

Examples of typical polyunsaturated or cross-linking comonomers or cross-linking agents are allyl (meth) acrylate, lower alkylene glycol di(meth)acrylate, poly(lower alkylene) glycol di(meth)acrylate, lower alkylene di(meth) acrylate, divinyl ether, divinyl sulfone, di- and trivinylbenzene, trimethylolpropane tri(meth)acrylate, pentaerythritol tetra(meth)acrylate, bisphenol A di(meth) acrylate, methylenebis(meth)acrylamide, triallyl phthalate and diallyl phthalate.

The present invention is further explained with reference to specific embodiments in the following examples. All temperatures are given in Degrees Centigrade.

EXAMPLE A-1

(Preparation of amino-terminated poly-N-vinyl-2-pyrrolidone)

Distilled N-vinyl-2-pyrrolidone (NVP) 55.58 g (0.50 Mol), 2-aminoethanethiol (Cysteamine) 2.33 g (30 mmol), and azo-bisisobutyronitrile (AIBN) 0.74 g (4.5 mmol) are mixed with 100 ml of absolute ethanol in a 350 ml three-neck flask, equipped with a mechanical stirrer, a reflux condenser and thermometer. The flask is then evacuated to a pressure of 600 mbar and a slow stream of nitrogen is used to deoxygenate the solution. This step is repeated 10 times. The solution is then heated to 60° C. After 28 hours of stirring at 60° C. under a nitrogen atmosphere, the solution is cooled to room temperature and stirred under nitrogen for a further 12 hours. The amino-terminated polymer is precipitated from 2 liter of anhydrous ethyl ether. The solid is dissolved in 200 ml of THF, and this reprecipitation is repeated twice. The white solid, 12.32 g (23% yield) is dried under reduced pressure for 48 hours and analyzed. The $M_W$ of the polymer is about 71,000, amino titration of the telomeric product is found to be 0.014 mVal/g.

EXAMPLE A-2

Preparation of a polyvinyl alcohol with pendant amino groups. PVA of $M_W$~18,000, carrying approximately 9 amino groups per chain was prepared in accordance with the first reaction step of Example 6 in EP-A-641 806. Consequently a 10% PVA-solution (Moviol 4-88, Hoechst) are mixed with 2.4 g (14.8 mmol) aminobutyraldehyde-diethylacetal (Fluka) and 20 g hydrochloric acid (37%). This mixture is stirred for 48 hours at room temperature. Subsequently said solution is neutralized with an aqueous (10% wt.) sodium hydroxide solution. This solution contains the title compound.

EXAMPLE A-3

(Macromer Synthesis)

51.5 g (50 mmol) of the perfluoropolyether Fomblin, ZDOL (from Ausimont S.p.A., Milan) having a mean molecular weight of 1030 g/mol and containing 1.96 meq/g of terminal hydroxyl groups according to end-group titration is introduced into a three-neck flask together with 50 mg of dibutyltin dilaurate. The flask contents are evacuated to about 20 mbar with stirring and subsequently filled with argon. This operation is repeated twice. 22.2 g (0.1 mol) of freshly distilled isophorone diisocyanate kept under argon are subsequently added in a counterstream of argon. The temperature in the flask is kept below 30° C. by cooling with a waterbath. After stirring at overnight room temperature, the reaction is complete. Isocyanate titration gives an NCO content of 1.40 meq/g (theory: 1.35 meq/g).

202 g of the α,ω-hydroxypropyl-terminated polydimethyl-siloxane KF-6001 from Shin-Etsu having a mean molecular weight of 2'000 g/mol (1.00 meq/g of hydroxyl groups according to titration) are introduced into a flask. The flask contents are evacuated to approx. 0.1 mbar and filled with argon. This operation is repeated twice. The degassed siloxane is dissolved in 202 ml of freshly distilled toluene kept under argon, and 100 mg of dibutyltin dilaurate (DBTDL) are added. After complete homogenization of the solution, all the perfluoropolyether reacted with isophorone diisocyanate (IPDI) is added under argon. After stirring overnight at room temperature, the reaction is complete. The solvent is evaporated under a high vacuum at room temperature. Microtitration shows 0.36 meq/g of hydroxyl groups (theory 0.37 meq/g). 13.78 g (88.9 mmol) of 2-isocyanatoethyl methacrylate (IEM) are added under argon to 247 g of the α,ω-hydroxypropyl-terminated polysiloxane-perfluoropolyether-polysiloxane three-block copolymer (a triblock copolymer on stoichiometric average, but other block lengths are also present). The mixture is stirred at room temperature for three days. Microtitration then no longer shows any isocyanate groups (detection limit 0.01 meq/g). 0.34 meq/g of methacryloyl groups are found (theory: 0.34 meq/g).

The macromer prepared in this way is completely colorless and clear. It can be stored in air at room temperature for several months in the absence of light without any change in molecular weight.

EXAMPLE A-4

(Preparation of a Contact Lens)

13.0 g of the macromer from Example A-3 are dissolved in 5.6 g of ethanol (Fluka, puriss. p.a.) (70% by weight solution). After complete homogenization of the solution, 5.2 g of 3-tris(trimethylsiloxy)silylpropyl methacrylate (TRIS from Shin-Etsu, product No. KF-2801), 7.8 g of freshly distilled N,N-dimethylacrylamide (DMA) and 160 mg of the photoinitiator Darocur®1173 (Ciba) are added. This solution is filtered through a Teflon membrane having a pore width of 0.45 μm under an argon pressure ranging from 1 to 2 atm. The filtered solution is frozen in a flask in liquid nitrogen, the flask is evacuated under a high vacuum, and the solution is returned to room temperature with the flask sealed. This degassing operation is repeated twice. The flask containing the macromer/comonomer solution is then transferred into a glove box with an inert-gas atmosphere, where the solution is pipetted into dust-free contact-lens molds made from polypropylene. The molds are closed, and the polymerization reaction is effected by UV irradiation (15 mW/cm$^2$, 5 min.), with simultaneous crosslinking. The molds are then opened and placed in ethanol, causing the resultant lenses to swell out of their molds. The lenses are extracted for 24 hours with constantly replenished distilled dichloromethane and subsequently dried in a high vacuum. The dried lenses are equilibrated in phosphate-buffered physiological saline solution in autoclave-resistant vials and then autoclaved at 120° C. for 30 minutes. All physical data measurements are carried out on autoclaved lenses.

The lenses produced in this way are characterized by the following values: oxygen permeability (Dk) 77 barrer (determined by the "wet" method described above), water content of the equilibrated lenses 32% by weight, elongation at break at 35° C. 360% modulus of elasticity 30° C. 0.5 MPa (measured using a Minimat from Polymer Laboratories, UK).

EXAMPLE A-5

(Preparation of 8-aminooctyl Iactobionic Acid Amide)

A suspension of 40 g (0.12 Mol) of lactobionolactone (Solvay, Germany) in 400 ml of methanol is added to a solution of 22 g (0.15 Mol) of 1,8-diaminooctane in 200 ml of methanol stirring in a three-neck flask equipped with a thermometer, a mechanical stirrer and a reflux condenser. After 24 hours of reflux under a nitrogen atmosphere, 5 g of activated charcoal is added to the flask and after 5 minutes of stirring the solution is filtered through a 1 cm thick layer of silica gel and hyflo. The slightly yellow solution is then concentrated upon evaporation to a volume of about 100 ml and after cooling to about 5° C., 20 ml of acetonitrile and 20 ml of diethyl ether are added to initiate crystallization. After 3 days of standing at 5° C., the crystalline product is filtered off and dried under a reduced pressure for 12 hours.

|  | % C | % H | % N |
| --- | --- | --- | --- |
| Calculated | 49.58 | 8.32 | 5.78 |
| Found | 49.68 | 7.99 | 5.56 |

Titration of amino groups: 1.80 mVal/g (titration with 0.1 N $HClO_4$).

EXAMPLE A-6

5-aminopentyl-β-cyclodextrin is prepared in accordance with the procedure described in example 16 of patent application WO 95/03336 (S. Hanessian).

EXAMPLE A-7
(Macromer Synthesis)

Reaction of β,ω-bis-3-aminopropyl-dimethylpolysiloxane with D(+)gluconic acid δ-lactone:

Before the reaction, the amino-functionalized polydimethylsiloxane employed for the synthesis (X-22-161-C, Shin Estu, JP) was finely dispersed in acetonitrile, extracted and then subjected to distillation in a thin layer evaporator at $10^{-4}$ Torr.

The following reactions take place with exclusion of $H_2O$. 200 g of purified amino-functionalized polydimethylsiloxane (0.375 meq of $NH_2$/g; Mn(VPO) 3,400–3,900 (VPO, Vapor Pressure Osmometry)), dissolved in 200 ml of absolute THF, are slowly added dropwise to a suspension of 13.35 g (75 mmol) of D(+) gluconic acid δ-lactone in 50 ml of absolute THF, and the mixture is stirred at 40° C. for about 24 hours until the lactone has reacted completely. (Monitoring of the reaction by thin layer chromatography (TLC): silica gel; i-propanol/$H_2O$/ethyl acetate 6:3:1; staining with Ce(IV) sulfate/phosphoromolybdic acid solution (CPS reagent)). The reaction mixture is then concentrated to dryness and the residue is dried at 0.03 mbar for 48 hours. 213.3 g of β,ω-bis(3-gluconamidopropyl)-polydimethylsiloxane are obtained. Titration of the amino groups with perchloric acid shows a conversion of the amino groups of 99.8%.

Reaction of β,ω-bis-(3-gluconamidopropyl)-dimethylpolysiloxane with IEM

The product obtained above (213.3 g) is dissolved in 800 ml of absolute THF and the solution is heated to 40° C. followed by the addition of catalytic amounts of dibutyltin dilaurate (DBTDL). 14 g (90 mmol) of IEM dissolved in 20 ml of absolute THF are added dropwise to this solution over a period of about 4 hours. This corresponds to a concentration of 1.2 equivalents of IEM per gluconamide unit. The reaction is carried out in the course of 48 hours (monitoring of the reaction by IR spectroscopy detection of the NCO bands). The reaction mixture is concentrated and the product is dried in a brown glass flask under 3 Pa (0.03 mbar) for 24 hours, while cooling with ice. 227.2 g of a colorless rubbery and elastic product of high optical transparency are obtained.

EXAMPLE A-8
(Preparation of a Contact Lens)

Before polymerization, the acrylic monomers employed, N,N-dimethylacrylamide (DMA) and 3-methacryloyloxypropyl-tris(trimethylsilyloxy)silane (TRIS) are each purified from inhibitors by distillation. 0.80 g (8.1 mmol) of DMA and 0.804 g (1.9 mmol) of TRIS are placed in a 50 ml round-bottomed flask, and the flask is flushed with $N_2$ for half an hour, while cooling with ice. 0.80 g of the macromer prepared according to Example A-7 are transferred to a round-bottomed flask with a nitrogen gas inlet, degassed under 3 Pa (0.03 mbar) for 24 hours and then dissolved in 2.7 g of ethanol which has been flushed with $N_2$ for half an hour beforehand. The subsequent preparation of samples and the polymerization are carried out inside a glove box under strict exclusion of oxygen. The above monomer mixture and the macromer solution are mixed, with the addition of 0.012 g (0.21 mmol) of Darocur®1173 and the mixture is subjected to microfiltration (0.45 μm filter). 180 μl of this mixture are introduced into polypropylene molds, which are then closed with an appropriate lid of polypropylene. The molds are then irradiated with a UV-A mercury high pressure lamp in a nitrogen atmosphere in a UV oven for 5 minutes. The lamps (5 each of the brand TLK 40W/10R, Philips) are located above and below the mold holder. The irradiation intensity is 14.5 mW/cm².

The polypropylene molds are then transferred to a laminar flow hood and opened. The finished lenses are released from the molds by soaking in a solvent mixture of methylene chloride and ethanol (2:3). The lenses are extracted in ethanol at room temperature in special polypropylene cages for 48 hours and then dried at 40° C. under 10 Pa (0.1 mbar) for 24 hours. Sterilization is accomplished by autoclaving at 120° C. for 30 minutes. The lenses obtained show an E modulus of 0.7 MPa, an oxygen permeability of 96 barrer and a hardness (Shore A) of 53.

EXAMPLE B-1
Plasma Induced Surface Graft Polymerization of 2-isocyanatoethyl methacrylate on Contact Lenses (Poly-IEM 1 coating)

The substrates including two contact lenses from Example A-4 and two lenses from Example A-8 are, after extraction in isopropanol and drying at 0.01 mbar, placed on convex glass holders (in order to expose the front curve of lenses and to shield the back curves of the lenses from any deposit) within the plasma reactor equipped with external ring electrodes. The distance between the substrates and the lower rim of the plasma zone is 12 cm. The reactor is evacuated to a pressure of 0.010 mbar, and held at these conditions for one hour. Then, the argon plasma gas flow rate into the plasma zone of the reactor is set to 20 sccm (standard cubic centimeters), the pressure in the reactor is adjusted to 0.07 mbar and the RF generator (27.12 MHz radio frequency generator, HFA Koppold & Co., Höhenkirchen, Germany) is switched on. The plasma discharge is maintained at a power of 170 Watts for a total period of 1 minute (in order to clear and activate the substrate surfaces). Afterwards, the IEM vapor carried by an argon gas stream is introduced into the reactor chamber from the IEM reservoir (maintained at 25° C.) at 0.15 mbar for 1 minute. After this, the following parameters for the plasma induced polymerization of IEM are chosen: Argon flow rate for plasma excitation=20 sccm, argon carrier gas flow rate for monomer (IEM) transport=10 sccm, temperature of the monomer (IEM) evaporation unit= 25° C., the distance between the lower rim of the plasma zone and the substrates=16 cm, the pressure=0.10 mbar, and plasma power=160 W. After 5 minutes of deposition, the plasma discharge is interrupted, the reactor is evacuated and maintained for 30 minutes at a pressure of 0.010 mbar. The reactor is then filled with dry nitrogen gas at atmospheric pressure. The lenses are then turned over, inserted into concave glass holders, and the whole procedure is repeated in order to coat the back side of the lenses.

The samples are then unloaded from the reactor and analyzed by ATR-FTIR measurements. Strong absorption bands at about 2270 cm$^{-1}$, illustrate the high OCN-surface functionality of the coated contact lenses.

EXAMPLE B-2
Plasma Induced Polymerization of 2-isocyanatoethyl methacrylate on Contact Lenses and on Ultrafiltration Membranes (Poly-IEM 2 Coating)

The substrates including 2 lenses from Example A-4, 2 lenses from Example A-8 and 2 pieces of polycarbonate filter membranes of a diameter of 25 mm (Poretics Corporation, Livermore, USA) are, after extraction in isopropanol, placed on a glass holder. The holder is positioned in the reactor at a distance of 16 cm from the lower edge of the plasma zone. The remaining steps are analogous to example B-1, namly:

Pretreatment: Pressure 0.010 mbar; 1 hour, argon plasma gas flow rate 20 sccm; pressure in the reactor is adjusted to 0.07 mbar and the RF generator is switched on. The plasma discharge at 170 W (1 minute).

Coating step: Argon flow for plasma excitation=20 sccm, argon carrier gas flow rate for monomer (IEM) transport=10 sccm, temperature of monomer (IEM) evaporation unit=25° C., the pressure=0.10 mbar, and the distance between the lower edge of the plasma zone and the substrates=15 cm. The graft polymerization is performed at a plasma power of 140 W for 5 minutes. At the end of the reaction period, the previous pressure of 0.010 mbar is restored and maintained for 30 minutes. The pressure is then brought to atmospheric pressure by using dry nitrogen.

The substrates are then turned over and the whole procedure is repeated to coat the other side of the substrates.

ATR-FTIR measurements show strong bands at about 2270 $cm^{-1}$, (N=C=O groups)

EXAMPLE B-3
Plasma Induced Polymerization of 2-isocyanatoethyl methacrylate (Poly-IEM 3 Coating)

In analogy to example B-2, the substrates including 2 lenses from Example A-4 and 2 lenses from Example A-8 are, after extraction in isopropanol, placed on a glass holder and positioned in the plasma reactor at a distance of 15 cm from the lower edge of the plasma zone. Pretreatment is identical to example B-2. Coating step conditions: Lenses repositioned at 25 cm from the lower edge of the plasma zone. IEM plasma induced polymerization in analogy to example B-2, at 160 W (5 minutes). Remaining steps identical to example B-2. Strong bands at about 2270 $cm^{-1}$ (ATR-FTIR spectroscopy).

EXAMPLE B-4
Plasma Induced Polymerization of 2-isocyanatoethyl methacrylate (Poly-IEM 4 Coating)

The substrates used for this coating are: 2 lenses from Example A-4, 2 lenses from Example A-8 and 2 pieces of PVP free polycarbonate membranes (Poretics Corporation, Livermore, USA) of a diameter of 25 mm. Pretreatment of the substrates in analogy to example B-3s wherein substrates at 15 cm from the lower edge of the plasma zone, pressure 0.012 mbar (40 min.), argon plasma gas flow rate 20 sccm, pressure in the reactor adjusted to 0.10 mbar and the RF generator is switched on (200 W for 1 minute). Coating steps : Repositioning of the substrates to 20 cm from the bottom of the plasma zone. IEM plasma induced polymerization in analogy to example B-3, at 180 W (5 minutes), pressure 0.2 mbar. At the end of the reaction period, the monomer vapor is further introduced in the postdischarge region for 15 minutes. Then the ground pressure of 0.012 mbar is re stored and maintained for 30 minutes. The remaining steps as in example B-1. Strong bands at about 2270 $cm^{-1}$ (ATR-FTIR spectroscopy).

EXAMPLE B-5
Plasma Induced Polymerization of Glycidyl Methacrylate (Poly-GMA Coating)

The substrates including 2 polycarbonate filter membranes of a diameter of 25 mm (Poretics Corporation, Livermore, USA) and 2 pieces of silicone film (Silastic,. Dow Chemicals) are, after extraction in isopropanol, placed on a moveable teflon holder. The holder is positioned in the plasma reactor at a distance of approximately 10 cm downstream from the edge of the visible plasma zone. After mounting samples, the system is pumped down to a pressure of 0.010 mbar, and held at these conditions for one hour. Then the argon plasma gas flow rate into the plasma zone o f the reactor is set to 20 sccm, the pressure in the reactor is adjusted to 0.15 mbar and the RF generator is switched on. The plasma discharge is proceeded at a power of 170 W for a total period of 1 minute. The plasma discharge is then interrupted and GMA vapor is introduced from the GMA reservoir (maintained at 30° C.) into the reactor at 0.25 mbar for 5 minutes. After this pretreatment period, the following parameters for the plasma induced grafting of the GMA are established: Argon flow for plasma excitation=10 sccm, argon carrier gas flow rate for monomer (GMA) transport= 10 sccm, temperature of monomer (GMA) evaporation unit=35° C., the pressure=0.35 mbar, and the distance between the lower edge of the plasma zone and the substrates=16 cm. The graft polymerization is performed at a plasma power of 150 W for 5 minutes. At the end of the reaction period, the GMA vapor is introduced in the post-discharged region for a further 5 minutes. The ground pressure of 0.010 mbar which is then restored and maintained for 30 minutes is brought to atmospheric pressure by using dry nitrogen.

The substrates are then turned over and the whole procedure is repeated to coat the other side of the substrates.

The samples are then unloaded from the reactor and analyzed by ATR-FTIR measurements. The absorption band at 1270 $cm^{-1}$ indicates the high epoxy surface functionality on all the samples.

EXAMPLE B-6
Plasma Induced Polymerization of Methacrylic Acid Anhydride (Poly-MAH Coating)

The substrates including two lenses from Example A4, and two lenses from Example A-8 are, after extraction in isopropanol, placed on the glass holder within the plasma reactor. Pretreatment identical to example B-5, with the proviso that GMA is replaced by MAH, and substrates at 12 cm.

Coating step is identical to example B-5, with the proviso that MAH reservoir is maintained at 30° C., substrates at 16 cm and plasma power=160 W (10 minutes). Remaining operations identical to example B-5.

ATR-FTIR analysis show bands at 1800 and 1760 $cm^{-1}$ (anhydride).

EXAMPLE B-7
Plasma Induced Polymerization of 4-vinyl-2,2-dimethyl Azlactone (VAL)

In analogy to the procedure disclosed in example B-2, Poretics polycarbonate ultrafiltration membranes were treated with VAL (ISOCHEM, Vert le Petit, France). Pretreatment (step 1) parameters are ajusted to: Argon plasma gas flow 20 sscm/min.; pressure 0.085 mbar; power 520 W; time 2 min.

The parameters for the plasma polymerization (step 2) are adjusted to: Argon carrier gas flux 10 sccm/min.; temp. of VAL source evaporator −15° C.; pressure 0.2 mbar; distance of sample from plasma zone 18 cm; reaction time 5 min.; power 375 W; pulsed plasma, frequency corresponding to 10:30 μsec (on:off time).

ATR-FTIR measurements show absorption bands at 1820 and 1770 cm$^{-1}$ (azlactone)

EXAMPLE B-8

In analogy to the procedure of example B-7, contact lenses of example A-4 were coated.

EXAMPLE C-1

Determination of N=C=O and azlactone group concentration on modified surfaces by the reaction with the spin label molecule 4-amino-2,2,6,6-tetramethyl-piperidine-1-oxyl (4-amino-TEMPO). Ten IEM plasma modified contact lens and ultrafiltration membranes (Poretics™, a polycarbonate material) samples from the examples indicated infra are soaked in a solution of 0.05 g of 4-amino-TEMPO (Fluka 09465) dissolved in a mixture of 1 ml of water and 4 ml of isopropanol. The isocyanate groups on the substrate surfaces are reacted with the spin label compound at 25° C. for 4 hours. The substrates are then washed 3 times in the same mixture solvent (i-propanol/water 4:1) and extracted for 12 hours in isopropanol. After drying at a reduced pressure of 0.010 mbar, the substrates are analyzed by ESR spectroscopy.

Concentration of spin label molecules on subtrate surfaces:

| Substrate from Example | Coating from Example | Concentration · 10$^{-9}$ Mol spin/cm$^2$ |
|---|---|---|
| contact lenses | | |
| A-4 | B-1 | 4.09 |
| A-8 | B-1 | 2.65 |
| A-4 | B-2 | 4.96 |
| A-8 | B-2 | 2.65 |
| A-4 | B-3 | 6.99 |
| A-8 | B-3 | 4.18 |
| A-4 | B-4 | 7.57 |
| A-8 | B-4 | 7.66 |
| A-4 | B-8 | 2.20 |
| membranes | | |
| Poretics | B-4 | 10.76 |
| Poretics | B-2 | 3.89 |
| Poretics | B-7 | 1.90 |

EXAMPLE C-2

Coupling reaction of isocyanate functionalized substrates with Bovine Serum Albumin. Three lenses from Example A-4 and 3 contact lenses from Example A-8 are surface modified with IEM according to the procedure described in Example B-4. The isocyanate functionalized contact lenses are then reacted with Bovine Serum Albumin (BSA) by immersing each lens in 3 ml aqueous solution containing 30 mg BSA at 25° C. for 16 hours. Following the albumin treatment, the lenses are extracted for 12 hours with ultra pure water to remove unreacted albumin. After this, the lenses are analyzed by ATR FTIR and contact angle measurements.

| Contact Lenses from Example: | A-4 | A-8 |
|---|---|---|
| | Contact angles | |
| Advancing angle (Adv.) | 26 | 49 |
| Receding angle (Rec.) | 19 | 43 |
| Contact angle Hysteresis (Hyster.) | 7 | 6 |

The FTIR-ATR spectra confirm the complete conversion of the OCN-groups due to the absence of an absorption at 2270 cm$^{-1}$.

EXAMPLES C-3–C-7

Coupling reactions of isocyanate functionalized substrates with other proteins. Substrates from Example A-4 and substrates from Example A-8 are surface functionalized with isocyanate groups as described in Example B-4. The functionalized substrates are then soaked in 1% aqueous solutions of various proteins to provide the coupling reactions in accordance with the procedure in Example C-2. After extraction in HPLC water the substrate surfaces are analyzed by ATR FTIR spectroscopy and contact angle measurements.

Contact angles on substrates modified by plasma induced polymerization and subsequent reactions with proteins (Examples C-3–C-7) are shown in Table 1.

TABLE 1

| Example | Substrate from Example No. | Protein used | Contact angle [°] Adv/Rec./Hyster. | Coupling* with OCN groups |
|---|---|---|---|---|
| C-3 | A-4 | Hirudin | 21/11/14 | quantitative |
| | A-8 | (Ciba-Geigy) | 38/25/13 | quantitative |
| C-4 | A-4 | Collagen III, | 43/28/15 | quantitative |
| | A-8 | from calf skin (Sigma) | 53/41/12 | quantitative |
| C-5 | A-4 | Mucin II, | 19/12/7 | quantitative |
| | A-8 | from porcine stomach (Sigma) | 23/14/9 | quantitative |
| C-6 | A-4 | Mucin I-S, | 57/19/38 | quantitative |
| | A-8 | from bovine submaxillary glands | 52/28/24 | quantitative |
| C-7 | A-4 | Elastin | 53/33/20 | quantitative |
| | A-8 | bovine neck (Fluka) | 55/31/24 | quantitative |

*confirmed by FTIR-ATR spectroscopy

EXAMPLE C-8

Coupling reaction of isocyanate functionalized substrates with Jeffamine ED 2001. Two contact lenses from Example A-4 and 2 contact lenses from Example A-8 are isocyanate functionalized as in Example B-4. Each lens is then individually soaked in 3 ml aqueous solution of Jeffamine ED 2001 (Texaco, USA) having a concentration of 10 mg Jeffamine/1 ml water. The coupling reaction is allowed to proceed overnight (16 hours) at room temperature. The substrates are then carefully rinsed with distilled water, extracted for 12 hours with ultra pure water and analyzed by ATR-FTIR and contact angle measurements.

| Substrate from Example: | A4 (B-4) | A-8 (B-4) |
|---|---|---|
| Contact angles: Adv./Rec./Hyster.: | 53/28/25 | 53/20/33 |

EXAMPLES C-9–C-11

Coupling reactions of isocyanate functionalized substrates with other polymers. The process described in Example C-8 is repeated for coupling reactions of isocyanate functionalized substrates with other amino-containing polymers listed infra. Contact angles measured on the modified substrates are summarized in Table 2.

TABLE 2

| Example | Substrate from Example | Polymer used | Contact angle [°] Adv./Rec./Hyster. |
|---|---|---|---|
| C-9 | A-4 | Amino-terminated | 36/4/32 |
|  | A-8 | PVP (Example A-1) | 25/7/18 |
| C-10 | A-4 | PVA with pendant | 27/21/6 |
|  | A-8 | amino groups (Example A-2) | 44/38/6 |
| C-11 | A-4 | Polyethyleneimine | 73/62/11 |
|  | A-8 | (Fluka) | 66/51/15 |

EXAMPLE C-12 AND C-13

The process described in Example C-8 is repeated for coupling reactions of isocyanate functionalized substrates with amino-cyclodextrin (example A-6) and aminooctyl-lactobionolactone-amide (example A-5) respectively. Contact angles measured on the modified substrates are summarized below.

| Substrate from Example: | A-4 | A-8 |
|---|---|---|
| Contact angles (example A-6): Adv./Rec./Hyster.: | 73/38/35 | 78/40/38 |
| Contact angles (example A-5): Adv./Rec./Hyster.: | 84/42/42 | 79/41/38 |

EXAMPLE C-14

Determination of glycidyl and anhydride group concentration with 4-amino-TEMPO. Two plasma modified substrates from Examples B-5 and 2 plasma modified substrates from Example B-6 are soaked in a solution of 0.05 g of 4-amino-TEMPO dissolved in a mixture of 1 ml of water and 4 ml of isopropanol. The reactive groups on the substrate surfaces are reacted with spin label molecules at 25° C. for 4 hours. The substrates are then washed 3 times in the same solvent mixture (i-propanol/water 4:1) and extracted for 12 hours in isopropanol. After drying at a reduced pressure of 0.010 mbar, the substrates are analyzed by ESR spectroscopy, upon which the concentration of spin label molecules is determined on lens surfaces.

| Substrate from example | Coating from example | Concentration · $10^{-9}$ Mol spin/cm$^2$ |
|---|---|---|
| Silastic Film | B-5 | 2.45 |
| Poretics membrane | B-5 | 2.60 |
| A-4 contact lens | B-6 | 7.52 |
| A-8 contact lens | B-6 | 4.32 |

EXAMPLE C-15

Coupling reaction of glycidyl and anhydride functionalized substrates. 2 plasma modified substrates from Example B-5 and 2 plasma modified substrates from Example B-6 are separately soaked in a solution of 0.1 g of Jeffamine ED 2001 dissolved in 5 ml of acetonitrile. The reaction is carried out at 25° C. for 4 hours. Then the substrates are first washed and then extracted in acetonitrile for 12 hours. After drying at a reduced pressure of 0.010 mbar for 3 hours, the substrates are analyzed by ATR FTIR and contact angle measurements. Contact angles measured on the modified substrates are summarized below:

| Substrate from Example: | Poretics ™ membrane B-5 | Silastic ™ film B-5 | A-4 contact lens B-6 | A-8 contact lens B-6 |
|---|---|---|---|---|
| Contact angles: Adv./Rec./Hyster.: | 69/31/38 | 74/29/45 | 77/44/33 | 79/31/48 |

Silastic ™, silicon film (Dow Chemicals)

EXAMPLE C-16–C-18

Coupling reaction of azlactone functionalized substrates. Lenses obtained from example B-8 are treated with 5% wt. aqueous solutions of amino-functional reagents indicated infra for 3 hrs at room temperature. Work up in accordance to example C-8.

| Example | "Amino"-Reagent | Contact Angles Adv./Rec./Hyster.: |
|---|---|---|
| C-16 | Polyethylene-imine, MW 60'000 Aldrich | 73/48/25 |
| C-17 | Jeffamine 2005 (Texaco) | 69/58/11 |
| C-18 | Diamino-polyethylene-glycol MW 600 (Fluka) | 41/29/12 |
| Comparative | None (Uncoated lens of example A-4) | 103/79/24 |

EXAMPLE C-19

284 mg of the oligopeptide H(Gly-NLeu-Pro)$_9$-NH$_2$.TFA (15 H$_2$O) are dissolved in 5 ml water. Adjusting the pH to 7.4 by addition of 0.1 N NaOH. Ethanol (0.3 ml) is added and the solution is filtered through a 0.22 µm membrane. This clear and sterile solution is used for treating the substrates of example B-7, wherein the treatment process is in analogy to example C-2. After this, the substrates are analyzed by ATR-FTIR.

EXAMPLE C-20

In analogy to example C-19, two substrates of example B-7 are treated at 5° C. with an aqueous solution of bovine collagen for 16 hrs. The bovine solution is prepared from 5 ml Vitrogen 100™ (Collagen Biomaterials Inc., Palo Alto Calif.) by adding 0.625 ml phosphate buffered saline, 0.625 ml 0.1 N NaOH and 3 drops 0.1 N HCl. Again, the substrates are analyzed by ATR-FTIR.

What is claimed is:

1. A method of preparing an article comprising a substrate with a polymer coating carrying reactive groups on its surface, wherein said polymeric coating comprises repeating units derived from a polymerizable unsaturated compound carrying a reactive group selected from the group consisting of isocyanato, isothiocyanato, glycidyl, anhydride, azlactone and lactone groups, wherein in said coating the concentration of said reactive groups is, based on spin label determination by ESR spectroscopy, in a range of $0.2–20 \cdot 10^{-9}$ Mol spin/cm2, wherein said coating is obtained by carrying out an after-glow plasma-induced polymerization of a polymerizable unsaturated compound carrying a reactive group selected from the group consisting of isocyanato, isothiocyanato, glycidyl, anhydride, azlactone and lactone groups on a substrate wherein the substrate is positioned at a distance of 4 to 40 cm and an inlet for said polymerizable unsaturated compound at a distance of 3 to 35 cm downstream outside of a plasma zone.

2. A method according to claim 1, wherein the plasma-induced polymerization is induced by a direct current (DC), a radio frequency (RF) or a microwave (MV) plasma.

3. A method according to claim 2, wherein the plasma-induced polymerization is induced by a RF plasma with inductive coupling.

4. A method according to claim 2, wherein the radio frequency is 13.56 or 27.12 MHz.

5. A method according to claim 1, wherein the plasma-induced polymerization is induced by a pulsed plasma.

6. A method according to claim 1, wherein the substrate is positioned at a distance of 8 to 30 cm downstream from the plasma zone.

7. A method according to claim 1 wherein the inlet is positioned at a distance of 6 to 25 cm downstream from the plasma zone.

8. A method according to claim 1, wherein the article is an ophthalmic device for vision correction, wherein the plasma-induced polymerization is carried out in the presence of the substrate that carries a removable patterned screen as a mask for the generation of imaged surfaces.

\* \* \* \* \*